United States Patent [19]

Urso

[11] Patent Number: 5,224,924
[45] Date of Patent: Jul. 6, 1993

[54] BACK TREATMENT DEVICE

[76] Inventor: Charles I. Urso, 54 Marivista Ave., Waltham, Mass. 02154

[21] Appl. No.: 749,873

[22] Filed: Aug. 26, 1991

[51] Int. Cl.⁵ .............................................. A61F 5/00
[52] U.S. Cl. ...................................... 602/19; 602/20; 135/71; 135/72; 135/73; 482/38; 482/42
[58] Field of Search .................. 135/68, 71, 72, 73; 297/411, 416; 128/78, 75; 482/38, 39, 40, 41, 42, 43, 139, 126, 907

[56] References Cited

U.S. PATENT DOCUMENTS

| | | | |
|---|---|---|---|
| 563,358 | 7/1896 | Burdick | 135/73 |
| 2,667,913 | 2/1954 | Dustin . | |
| 2,850,745 | 9/1958 | Cowell . | |
| 2,906,260 | 9/1959 | Myers | 128/78 |
| 3,063,752 | 11/1962 | Moore . | |
| 3,710,807 | 1/1973 | Ferry | 135/71 |
| 3,896,798 | 7/1975 | Simon | 482/41 |
| 4,565,409 | 1/1986 | Hollonbeck . | |
| 4,815,732 | 3/1989 | Mahvi | 482/907 |
| 4,996,978 | 4/1991 | Gingras . | |
| 5,011,139 | 4/1991 | Towley, III | 482/41 |
| 5,018,512 | 5/1991 | Dolan | 482/42 |
| 5,080,352 | 1/1992 | Freed | 482/41 |

FOREIGN PATENT DOCUMENTS

| | | |
|---|---|---|
| 23730/88 | 6/1989 | Australia . |
| 510854 | 3/1955 | Canada . |
| 2410839 | 9/1975 | Fed. Rep. of Germany . |
| 3415737 | 10/1984 | Fed. Rep. of Germany ........ 135/68 |
| 678693 | 10/1991 | Switzerland . |
| 599871 | 3/1948 | United Kingdom . |

OTHER PUBLICATIONS

"BackSaver" Catalogue, BackSaver Products Co., Holliston, Mass., 1992, 2 pages.

*Primary Examiner*—Richard J. Apley
*Assistant Examiner*—Lynne A. Reichard
*Attorney, Agent, or Firm*—Hamilton, Brook, Smith & Reynolds

[57] ABSTRACT

A back treatment device comprising a spaced pair of adjustable crutches (26L, 26R), for supporting the upper body of a user. Each crutch includes an air-inflatable underarm member (44) for comfort. A pair of forearm rests (140L, 140R) and a pair of padded handles (70L, 70R), all adjustable, are positioned such that a handle and rest are located laterally of a respective crutch. The three pairs are movably supported such that the user can be alternately supported on each pair or on combinations of pairs. A spring scale (90) is mounted between lower ends of the crutches such that the user sits on the scale while monitoring a conveniently located weight indicator. By slightly depressing his or her shoulders, the user uses the body support members (crutches, forearm rests, handles) to induce spinal traction. Feedback from the scale allows the user to accurately control the traction with minimum effort. Using the device takes pressure off of spinal discs while symmetrically strengthening supportive back muscles. Means are provided for securing a patient, lying on his back, to the device so that he can be lifted to an upright position while his upper body is supported by the device.

19 Claims, 6 Drawing Sheets

BACK TREATMENT DEVICE

TECHNICAL FIELD

This invention relates to devices for supporting the upper body of a seated person and more particularly to devices by which spinal traction can be induced in a person seated upright.

BACKGROUND

Treatment for common back ailments, including slipped or herniated disc, generally includes a lengthy period of immobilization in a firm bed. If adhered to, the treatment can be effective but is difficult to carry through. As result of the extreme inconvenience and boredom of horizontal immobilization, patients will often ignore the advice of their physicians and get out of bed for meals and diversions. Such activities with upper body weight on a damaged disc, especially as the spine bends or twists, may result in slowed healing or further damage. On the other hand, days or weeks of total bed rest may cause supportive back muscles to loose strength. Lack of fitness of back muscles can be a predisposing factor to back ailments.

The subject invention provides a valuable adjunct to bed rest in the treatment of disc injury and other back ailments. With the device, a patient can sit upright while in accurately controlled spinal traction. The device also allows the patent to strengthen and tone back muscles while maintaining back symmetry. Further, the patient's arms and hands can be free for using eating utensils, writing, or playing board games while in treatment.

SUMMARY OF THE INVENTION

The present invention comprises a spaced pair of adjustable crutches for supporting the upper body of a patient. Each crutch includes an air-inflatable underarm member for comfort. A pair of forearm rests and a pair of padded handles, all adjustable, are positioned such that a handle and rest are located laterally of a respective crutch. The three pairs are movably supported such that the user can be alternately supported on each pair or on combinations of pairs. A spring scale is mounted between lower ends of the crutches such that the patient sits on the scale while monitoring a conveniently located weight indicator. By slightly depressing his or her shoulders, the patient uses the body support members (crutches, forearm rests, handles) to induce spinal traction. Feedback from the scale allows the patient to accurately control the traction with minimum effort. Using the device takes pressure off of spinal discs while symmetrically strengthening supportive back muscles. Means are provided for securing a patient, lying on his back, to the device so that he can be lifted to an upright position while his upper body is supported by the device.

Other advantages of the invention will become apparent from consideration of the drawings and ensuing description.

BRIEF DESCRIPTION OF THE DRAWINGS

The accompanying drawings in combination with the description herewith, illustrate features and advantages of the invention. Like reference numerals in different views refer to the same parts. The drawings are intended to illustrate principles of the invention and are not necessarily to scale and in which drawings.

DETAILED DESCRIPTION

Figure 1:
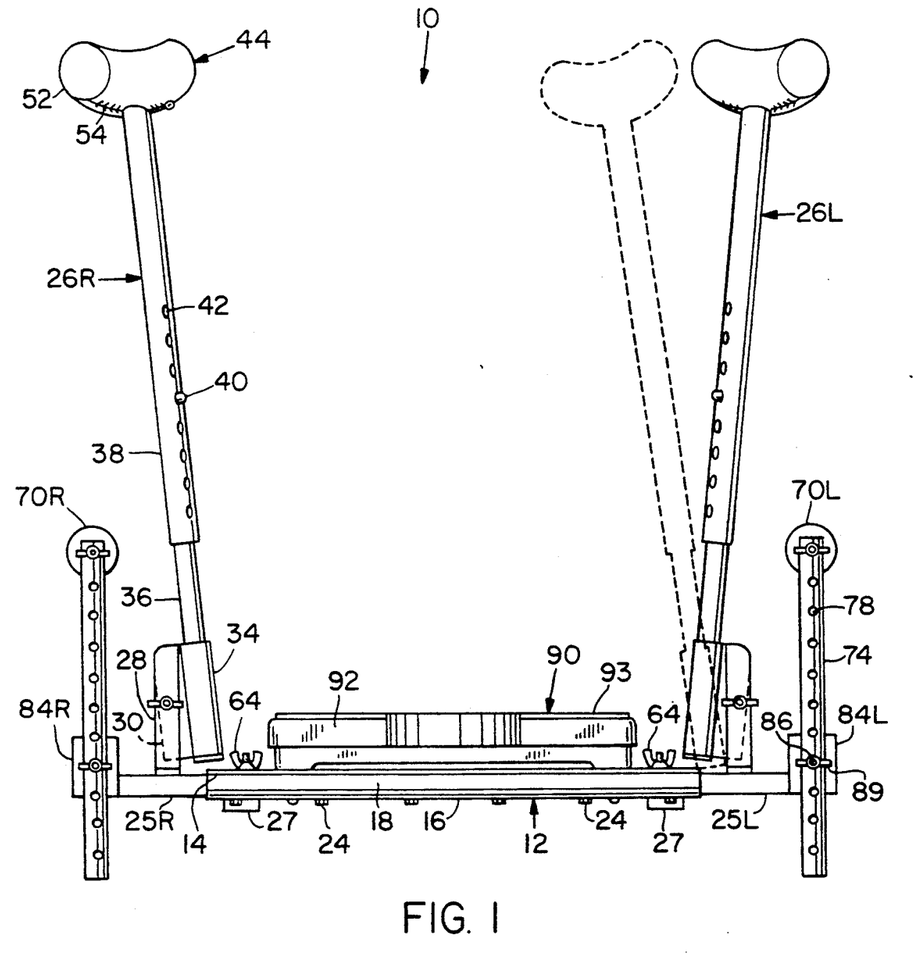
FIG. 1 is a front elevational view of a back treatment device constructed in accordance with the invention, parts being removed for clarity.

A back treatment device embodying the principles of this invention is identified generally by the numeral 10 in FIG. 1. The device comprises a shallow base 12 having spaced upper and lower rectangular aluminum plates 14, 16. Sandwiched between the plates are two fixed 1×4 inch hardwood boards 18, 20 (FIG. 4) which are spaced from each other. Countersunk flat head machine screws 22 (FIG. 4), passing through the base in bores 23, mate with nuts 24 (FIG. 1) to hold the base together.

Rubber pads 27, glued to the underside of the base, protect the surface of a chair (not shown) on which the treatment device may be placed for operation.

The spaced boards and plates define a track which runs longitudinally within the base. The track serves to slidably support two slidable elements 25L, 25R (FIG. 4, 6) comprising hardwood boards. Each element extending from left and right ends of the track, respectively, so that they can slide linearly toward and away from each other.

Figure 4:
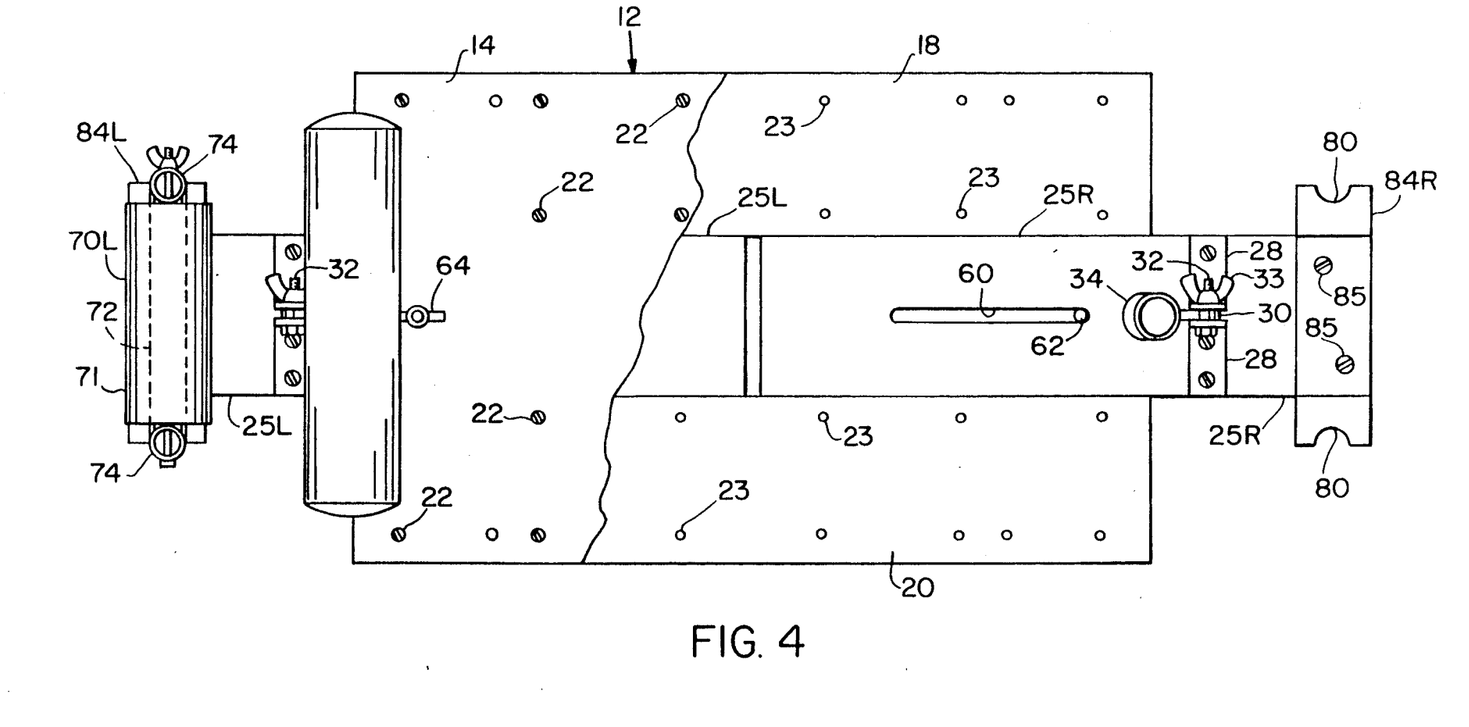
FIG. 4 is a fragmental top view of the device of FIG. 1, wherein more parts are removed.

Since each element 25L, 25R is similarly constructed, only one is described in detail. As shown in FIG. 4, element 25R includes a longitudinal slot 60 for receiving a screw 62 which passes vertically through a bore in the base 12. The screw 62 is mated to a wing nut 64 (FIG. 1, 6) which serves to lock the element in place after the same is slidably adjusted to a preferred position. Tightening the nut 64 depresses the plates slightly, thereby pressing the plates against the element sandwiched therebetween.

Figure 6:
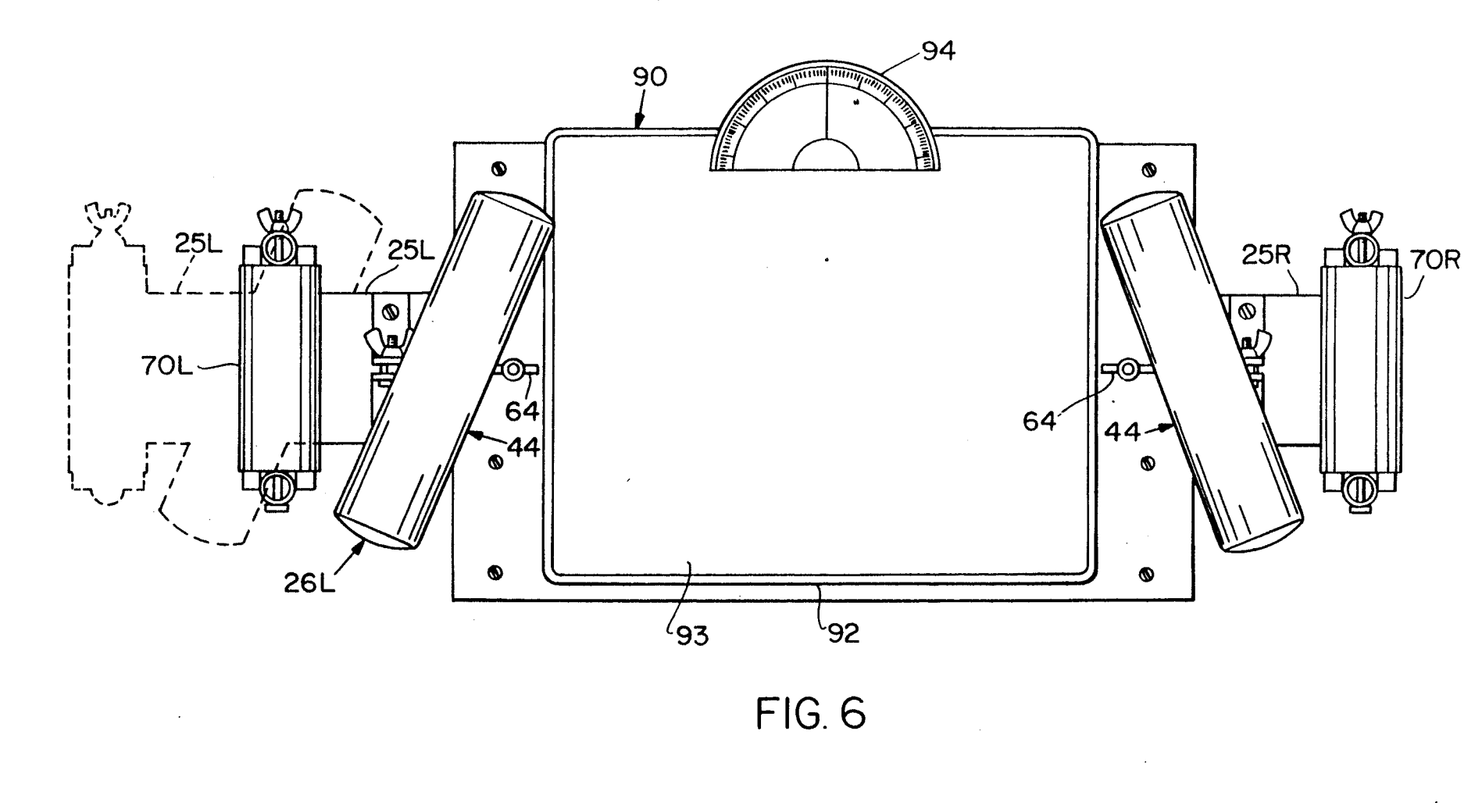
FIG. 6 is a top view of the device of FIG. 1, wherein some movable components are in different positions relative to their positions in FIG. 1.

As best seen in FIG. 1, a pair of adjustable crutches 26L, 26R are mounted on respective outer end portions of the slidable elements. Mounted on the ends of the elements, laterally of the crutches, are a pair of vertically adjustable handles 70L, 70R, respectively. Thus, the right crutch and right handle can slide linearly toward and away from the left crutch and left handle, and vice versa. FIG. 6 shows the left crutch 26L and left handle 70L in a laterally retracted position (solid image) and a laterally extended position (phantom image).

Since both crutches are similarly constructed and mounted, a detailed description is focused primarily on one crutch. The right crutch 26R includes an inner support tube 36 (FIG. 1) slidably mounted within an outer tube 38 such that the crutch is longitudinally extendible for vertical adjustment. The vertical adjusting means includes a row of holes 42 along tube 38 and a spring button 40, which extends from tube 36, for selectively locking into one of the holes. Other details of the vertical adjusting means are not shown since the method is conventional in crutches used for walking.

Figure 2:
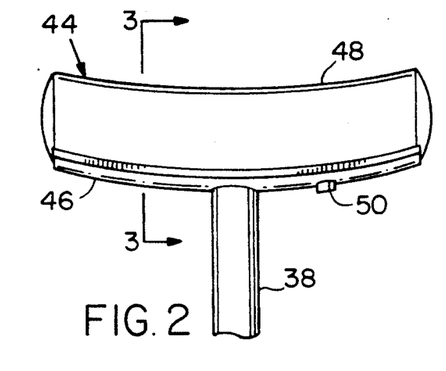
FIG. 2 is a fragmental side view in elevation of a crutch.
Figure 3:
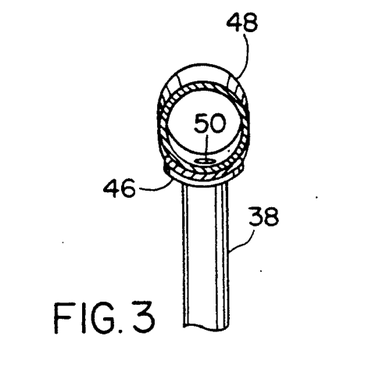
FIG. 3 is a fragmental end view in elevation, partly in section taken vertically along the line 3—3 of FIG. 2.

Mounted to an upper end of tube 38 is an underarm member 44 comprising an elongated rigid boat-like cradle 46 (FIG. 2, 3) welded to tube 38. The cradle includes a concave upper surface for receiving a sausage-shaped inflatable bladder 48 thereon. The underside of the elongated bladder conforms with the cradle. Bladder 48 is comprised of a curved rubber tube closed at both ends and is provided with a filling stem 50 which is similar to that of a football bladder. The stem extends through an aperture in the cradle so that the bladder can be inflated with compressed air introduced through the stem.

Covering the bladder and cradle is a sausage-shaped soft leather cover 52 (FIG. 1) installed by slipping the bladder and cradle through a longitudinal opening in the cover underside. Thus, the soft cover and bladder form an elongated inflatable cushion portion of the underarm member. Laces 54, threaded through lace holes in edge portions of the cover opening, tie the cover tightly in place.

The mounting means for crutch 26R includes a hollow cylindrical sleeve 34 which is closed at its bottom end. Sleeve 34 serves as a bearing which receives tube 36 to pivot therein. A pivot lug 30 extends laterally from the sleeve and is mounted to pivot between a pair of opposed L-shaped outer lugs 28 (FIG. 4) fixed to element 25R with screws. A pivot screw 32, on which lug 30 pivots, passes through aligned apertures in the lugs 28, 30. Wing nut 33 holds the screw 32 in place.

FIG. 1 shows the left crutch 26L in two limiting positions between which the crutch can pivot laterally; an inner position (phantom image) and an outer position (solid image). Hence, the crutches can adjust to a patient supported on the crutches. However, the crutches do not pivot forward or backward so that the patient's spinal column does not move. Each crutch can also pivot about its longitudinal axis as indicated by the relatively different positions of a crutch underarm member comparing FIG. 1, 4 and 6. Thus, when a patient is supported on the crutches, each underarm member adjusts as the patient moves his arms.

Both handles 70L, 70R are constructed and mounted in the same manner. Handle 70L is horizontally positioned and includes a cylindrical urethane foam pad 71 (FIG. 4) surrounding a horizontal cylindrical core 72. Concave end portions of the core receive respective vertical support tubes 74 (FIG. 1, 4) which are attached thereto by a long screw passing through aligned holes in the core and tubes. Each support tube 74 includes a plurality of regularly spaced holes 78 passing horizontally through the tubes wherein the holes of one tube are aligned with those of the opposite tube.

Figure 5:
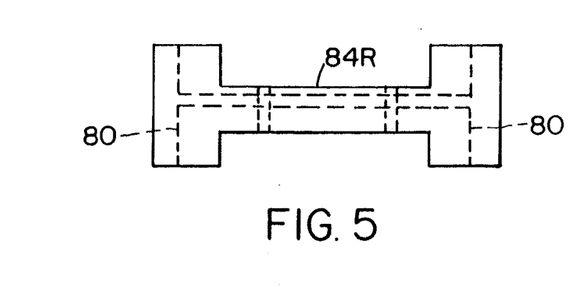
FIG. 5 is a side view in elevation of a track form.

The tubes 74 are slidably supported in a track form 84L. As can be understood from viewing form 84R in FIG. 4 and 5, the tubes are received in semi-circular tracks 80. Each track form is fixed to a respective element with screws 85 (FIG. 4). A long screw 86 (FIG. 1), passing through aligned tube holes and through the form, holds the tubes in place. A wing nut 89 holds the screw in place and allows easy removal of the screw to be selectively repositioned in another set of tube holes. Thus, the handle can be adjusted vertically to a preferred position.

Attached to each underarm member 44 (FIG. 7), is a respective over-the-shoulder strap 100. Each strap comprises front and back sections 102, 104, wherein each section is sewn to respective ends of an underarm member cover. Sewn to a distal end portion of each front strap section is a Velcro strip 106 for fastening to a mate Velcro strip 108 sewn to a distal end portion of each back strap section. Thus, the two sections of each strap can be detachably fastened together to form an arch over the shoulder of a patient to hold his shoulder on the associated underarm member.

Figure 7:
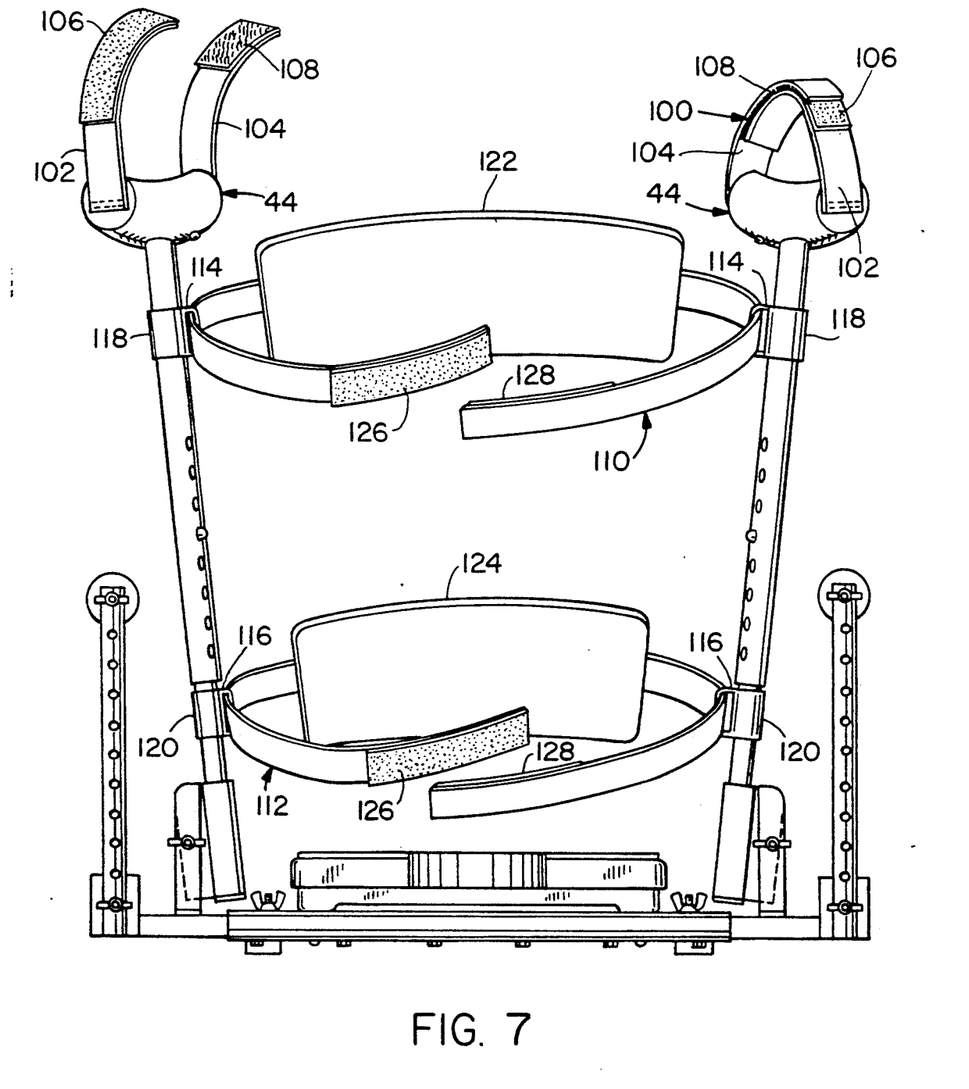
FIG. 7 is a front elevational view of the back treatment device of FIG. 1 with parts added including straps and belts.

Connected between the crutches are upper and lower belts 110, 112 which, in concert with the straps and semi-rigid back supports 122, 124 sewn to respective belts, secure the patient to the crutches. The belts are connected to the crutches by passing through belt loops 114, 116, respectively, which are fixed to sleeves 118, 120 that surround the crutch tubes. Each sleeve is slidable longitudinally of the tube therein so that the associated belt and back support can be adjusted longitudinally of a patient's spine. Mated Velcro strips 126, 128, sewn to respective distal end portions of the belts, provide a means of fastening the ends of the belts together to secure a patient.

Though Velcro is mentioned herein as a means of fastening the strap or belt ends, other conventional fastening means such as buckles, ties, clasps, hooks, etc., may be used.

Another pair of body supporting members which for clarity are shown added to the device in FIG. 8-11, rather than being included in FIG. 1. The pair comprise forearm rests 140L, 140R, each resembling half of a longitudinally divided hollow cylinder. Each rest includes a rigid outer portion 141 lined on its concave side with a resilient pad 142 which may be foam rubber or plastic foam. The concave surface is intended for receiving and approximately conforming to the underside of the user's forearm.

Each forearm rest is positioned laterally of a respective crutch, below the underarm member. The support means for each rest includes an inner tube 144 capped with a pipe cap 146 welded to an upper end portion of the tube. A screw, passing through aligned apertures in the forearm rest and cap, is mated with a nut 148 (FIG. 9) to hold the components together. A spring 150, inside the tube, compressed between the cap and nut, urges the forearm rest in contact with the cap. As arranged, the forearm rest can pivot about its first pivotal axis, the longitudinal axis of its support means.

The inner tube 144 is slidably received in an outer tube 152 which includes opposing rows of spaced holes 154. A pair of conventional spring buttons 156, extending from the inner tube, are receivable in any selected pair of aligned holes to provide a means for adjusting the height of the forearm rest relative to an associated underarm member.

The lower end portion of the outer tube is capped by a pipe cap 158 welded thereon. Cap 158 is fixed to the center of a U-shaped bracket 160 by a fastener such as a screw or rivet passing through the cap and bracket. The two legs of the bracket are pivotally mounted to lateral sides of respective tubes 74 such that the bracket straddles the tubes and handle. Distal end portions of the bracket legs have aligned apertures which receive the long screw passing through the handle and tubes 74. The bracket pivots on the long screw so that a second pivotal axis of the forearm rest and the pivotal axis of its support means are in common with the longitudinal axis of the handle.

Figures 8, 9:
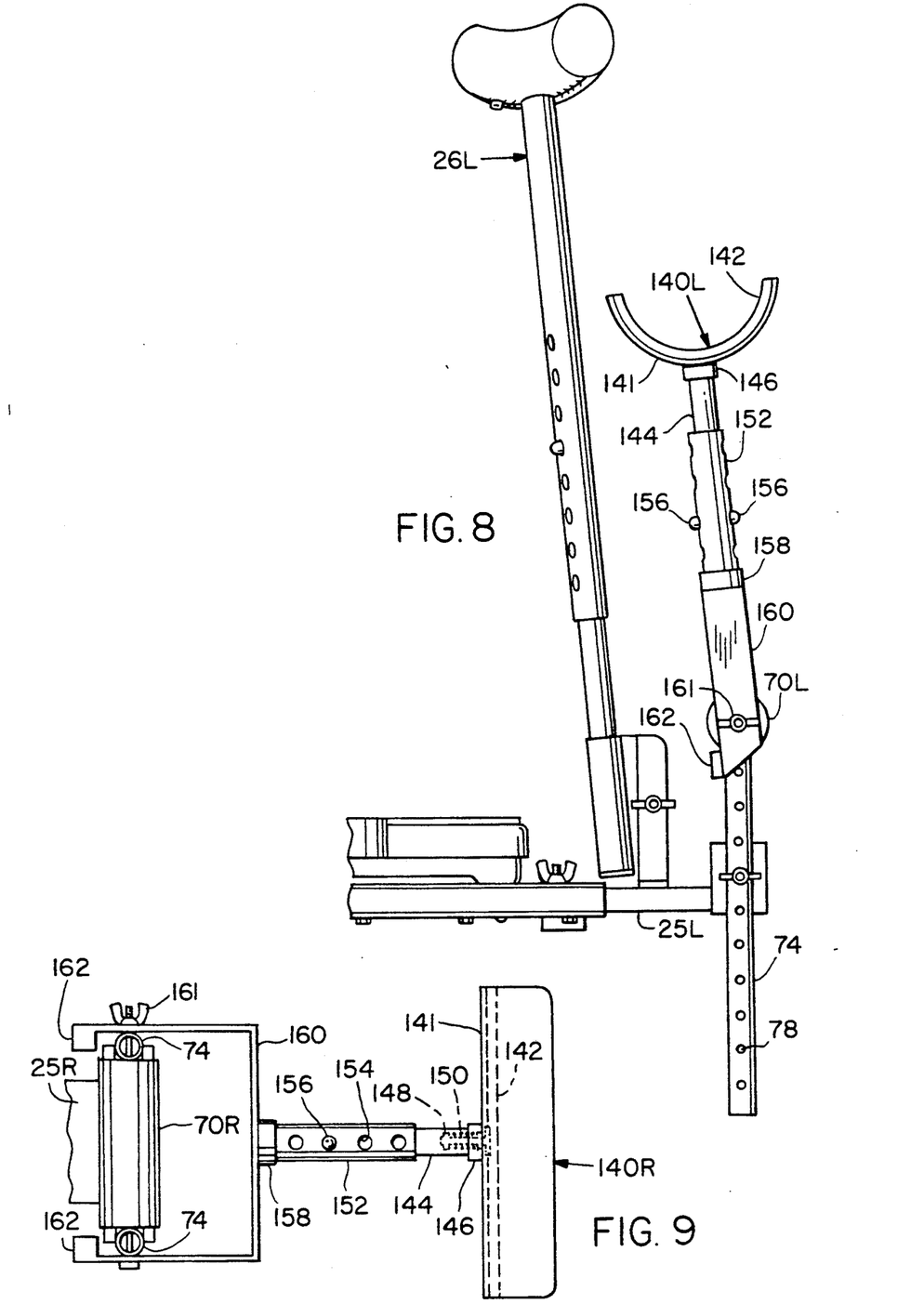
FIG. 8 is a fragmental front view in elevation of the device of FIG. 1, with parts added including a forearm rest in an erect position.
FIG. 9 is a fragmental top view of the device of FIG. 1, with parts added including a forearm rest in a receded position.
Figures 10, 11:
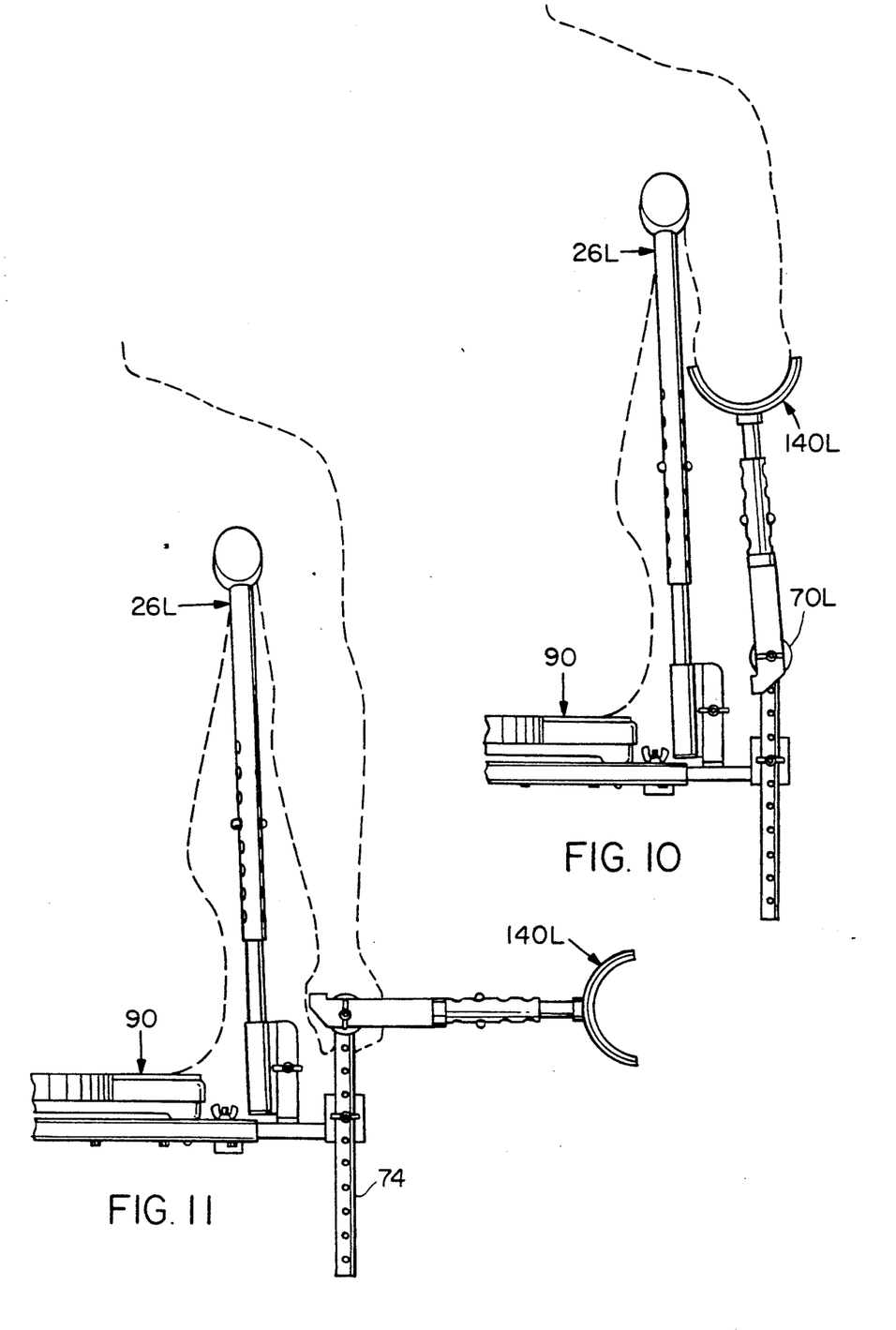
FIG. 10 shows the device of FIG. 8 in use.
FIG. 11 shows the device of FIG. 8 in use wherein the forearm rest is in the receded position.

Thus, each forearm rest (and its first pivotal axis) can move between an erect position above a respective handle (as shown in FIG. 8 and 10) and a receded position (as shown in FIG. 9 and 11). In the erect position, user body weight can be supported on the forearm rests. In the receded position, the forearm rests are cleared from hindering user access to the handles (forearm rests being positioned laterally of the handles). User body weight can then be supported on the handles. Further downward movement can position the forearm rests below tubes 74. Wing nut 161 can lock a respective rest at any preferred position.

To prevent a respective rest and its support means from exceeding the erect position, a pair of stops 162 contact tubes 74. The stops comprise inwardly directed tabs extending from one side of respective distal end portions of the bracket legs. In the erect position, the center of gravity of the forearm rest and its support means is biased toward the stop side of the bracket. This stabilizes the forearm rest so that locking with the wing nut is generally not necessary.

From the preceding description it can be understood that a forearm rest is pivotally supported to move laterally such that the longitudinal axis of the forearm rest moves about the second pivotal axis wherein the longitudinal and pivotal axes stay normally approximately horizontal as the forearm rest moves. Both forearm rests and their support means are similar in construction and function.

Mounted on the base 12, between the crutches and handles, is a conventional spring scale 90 (FIG. 1, 6). Screws, passing upwardly through the base and into the bottom side of the scale, connect the scale onto the base. Projecting forward from a platform 92 is an indicator 94 (FIG. 6) for displaying weight sensed by the scale. The scale is positioned relative to the combination such that the indicator projects anteriorly from the main body of the treatment device so that a user sitting on the device can easily see the indicator between the user's thighs.

Seat means comprising a resilient pad 93 is glued onto the scale. The seat means supports user weight sensed by the scale, which weight differs from the user weight supported on the body support members (crutches, forearm rests, handles).

Operation of the Invention

The back treatment device can be used on a bed or armless chair, such as a folding chair. If used on a bed, the handle support tubes 74 (FIG. 8) must be moved up to their highest positions. The handles and forearm rests can then be vertically adjusted by repositioning the screw mated to wing nut 161 at a preferred set of holes 78. In either case, the patient or user can sit on the scale, between the crutches.

The user upper body weight can be supported on the crutches (positioned under his upper arms) and/or on the handles with his hands positioned thereon. Alternatively, his upper body weight can be supported on the crutches and/or forearm rests. The objectives are to relieve the spine of upper body weight and, for some ailments, to accurately induce and maintain spinal traction. The latter is achieved by using the body support members (crutches, forearm rests, handles) in concert with feedback from the weight indicator 94, as explained hereinafter. The user can easily see the indicator between his thighs while maintaining upper body symmetry about his body midline.

The pair of crutches should be adjusted to accommodate the size of the user such that he can support his upper body weight on the crutches while sitting up straight.

The pair of handles should be adjusted such that, while being supported on the crutches, he can grip the handles, one in each hand, with his arms nearly fully extended (as indicated in FIG. 11). The forearm rests must be in the receded position. Optionally, the handles can be used for upper body support, without using the crutches, when the underarm members are lowered.

The pair of forearm rests can be adjusted to a distance of an upper arm's length below the underarm members user forearm on a respective forearm rest (in the erect position). Thus, user weight can be supported simultaneously on the underarm members and forearm rests (as indicated in FIG. 10). Optionally, with lowered underarm members, the user can be supported on the forearm rests without using the underarm members.

Hence, the user can be alternately supported on each pair by positioning the pairs relative to each other such that at least one pair at a time is in position to support the user, clear of hindrance to the user from the other pairs.

With the device properly adjusted, the user can enhance spinal traction by slightly depressing his shoulders while being supported on at least one pair of body support members. This causes an upward pull on the vertebrae and transfers additional upper body weight onto the body support members. The lower portions of the trapezius muscles, which are involved in the action, are large enough to make the effort easy.

Practically all weight can be off the lumbar discs by keeping the weight indicated by the scale at about the difference between his total body weight and the weight normally supported by his lowest lumbar disc. This difference is herein called the traction number or TN. For example, if his total body weight is 140 lbs. and the weight normally supported by his lowest disc is 60 lbs., the TN is 80 lbs. Thus, by monitoring the user weight sensed by the scale, the user can respondingly apply a portion of user weight to at least one pair of body support members resulting in an accurately controlled tractional force on the user's spine.

For convenience, the amount of the user's body weight supported on his lowest disc is herein called the LLD (load on lowest disc). A quick-reference chart could be attached to the device, by a manufacturer, for looking up the LLD weight corresponding to the user's height, total weight, and approximate frame size.

Feedback from the indicator allows accurate control of the tractional force with minimum effort. The user need only glance at the indicator occasionally and react if necessary. If he gets tired of using one pair of body support members, he can shift his LLD weight to a different pair or a combination of pairs (simultaneously using crutches and forearms rests or crutches and handles). When the user's hands need to be free, such as for eating meals, the crutches alone can support the LLD weight.

Even without depressing his shoulders, the body support members support a substantial amount of his upper body weight, thereby relieving his discs of that weight. Therefore, a slipped disc patient might be advised by his doctor to alternate between periods of just resting on the support members, and periods of making the slight effort to place the full LLD weight on the members. The resulting traction is particularly effective on the lumbar region of the spine. Herniation is most common in the lumbar discs with generally increased frequency toward the lower end of the region.

Patients with mild back ailments may be able to get on and off the treatment device on their own. Those with serious conditions, including hospitalized patients, might need assistance. If his condition warrants, a patient can be secured to the device while lying in bed on his back. After being secured, he can be lifted to an upright position while his upper body is being supported by the device. This can be done by using the straps and belts shown in FIG. 7.

Before securing a patient who is on his back, to the device, the belts should first be removed from the device. An assistant can slide belt 110 (FIG. 7) under the patient such that the upper back support is under the patient's upper back. Belt 112 can be slid under the patient such that the lower back support is under his lower back. By tilting the treatment device 90 degrees, it can be positioned with the scale against the patient's buttocks and the underarm members against respective armpits. Belt ends are then passed through the belt loops and fastened in front of the patent. The straps are fastened over his shoulders.

Secured to the device, the patient may then be lifted to an upright position for treatment with his legs over the edge of the bed. If preferred, by using the handles, two assistants can move the patient with the treatment device to a folding chair. With the patient in an upright position, the belts and straps may be unfastened and he can eat meals, tone muscles, etc., while in traction. Later, he can be secured again and lowered back to the reclined position while the treatment device supports his back. In the reclined position, the device can be removed by reversing the above-described steps.

While the above description contains many specificities, these should not be construed as limitations on the scope of the invention, but rather as an exemplifications of a preferred embodiment. Those skilled in the art will envision other possible variations that are within its scope. Accordingly, the scope of the invention should be determined not by the embodiment illustrated, but by the appended claims and their legal equivalents.

What is claimed is:

1. A body support device comprising:
a pair of handles supported in spaced relation for supporting user upper body weight on the handles, each handle having a longitudinal axis;
a pair of forearm rests for resting each user forearm on a respective rest in order to support user upper body weight on the rests; and
forearm rest support means for movably supporting each rest such that each forearm rest is movable about a respective handle longitudinal axis.

2. The body support device as defined in claim 1, wherein each forearm rest is slidably supported to be adjustable in distance from a respective handle.

3. A body support device comprising:
a pair of handles supported in spaced relation for supporting user upper body weight on the handles;
a pair of forearm rests for resting each user forearm on a respective rest in order to support user upper body weight on the rests; and
forearm rest support means for movably supporting each rest such that each forearm rest is supported on a pair of pivotally supported legs which straddle a respective handle.

4. The body support device as defined in claim 3, wherein each forearm rest is slidably supported to be adjustable in distance from a respective handle.

5. A body support device comprising:
a pair of underarm members for being positioned against respective armpits of a user in order to support user upper body weight on the members;
a pair of forearm rests for resting each user forearm on a respective rest in order to support user upper body weight on the rests;
a pair of handles, each for being held by the user in order to support user upper body weight on the handles; and
support means for movably supporting and connecting the members, rests, and handles together such that the user can be alternately supported on each pair, clear of hindrance to the user from the other pairs, each pair being supported to be free-standing.

6. A back treatment device comprising:
seat means for supporting a portion of the weight of a user;
a pair of body support members connected for supporting upper body weight of the user; and
a scale, for measuring weight, connected for determining user weight relieved from the seat means by the support members, the scale having a quantitative weight indicator positioned anteriorly of the back treatment devices so that the user can read the indicator.

7. The back treatment device as defined in claim 6, wherein the scale is connected to the seat means for sensing user weight on the seat means.

8. The back treatment device as defined in claim 6, wherein the weight indicator is positioned approximately equidistant from each operatively positioned body support member.

9. The back treatment device as defined in claim 6, wherein the weight indicator is positioned in the vicinity of an anterior portion of the seat means.

10. The back treatment device as defined in claim 6, wherein the body support members comprise a pair of underarm members for being positioned against respective armpits of the user in order to support user upper body weight on the underarm members.

11. The back treatment device as defined in claim 6, wherein the body support members comprise a pair of adjustably supported handles in spaced relation for being held by the user.

12. The back treatment device as defined in claim 11, wherein the handles are adjustably supported to move up and down and toward and away from each other.

13. The back treatment device as defined in claim 6, wherein the body support members comprise a pair of forearm rests supported in spaced relation for being positioned under respective forearms of the user.

14. A body support device comprising:
a pair of forearm rests for resting each forearm of a user on a respective rest in order to support user upper body weight on the rests; and rest support means for supporting the rests in a freestanding position, the rest support means having rest swivel means for pivotal movement of each rest about an erect pivotal axis so that each user forearm on each respective rest can move therewith about the erect pivotal axis.

15. The body support device as defined in claim 14, further comprising means for pivotally supporting each rest to be movable about a second pivotal axis which is transverse to the first pivotal axis.

16. The body support device as defined in claim 14, further comprising:
   seat means for supporting the buttocks of the user; and
   each rest being connected to the seat means and supported to be linearly movable relative to the seat means in an approximately horizontal direction.

17. The body support device as defined in claim 16, wherein each linearly movable rest is slidably supported.

18. A body support device comprising:
   a pair of crutches for being positioned against user armpits to support the user;
   a back support for being positioned against the user's back, the back support being supported on each crutch; and
   an upper back support supported on each crutch wherein at least one of the back supports is movably supported and movable relative to the other back support in order to be adjustable longitudinally of the user's spine.

19. A body support device comprising:
   a pair of crutches for being positioned against user armpits to support the user;
   a back support for being positioned against the user's back, the back support being supported on each crutch; and
   an upper back support supported on each crutch wherein both back supports are movably supported to be movable relative to each other and both back supports being adjustable longitudinally of the user's spine.

* * * * *